US005585505A

United States Patent [19]

Mulder et al.

[11] Patent Number: 5,585,505

[45] Date of Patent: Dec. 17, 1996

[54] HATCHING AGENT FOR THE POTATO CYST NEMATODE

[75] Inventors: Johan G. Mulder, Zwolle; Pieter Diepenhorst, Heesch; Pieter Plieger, Hoogeveen; Ingrid E. M. Brüggemann-Rotgans, Pijnacker, all of Netherlands

[73] Assignee: B.V. Chemische Pharmaceutische Industrie "Luxan" , PA Elst, Netherlands

[21] Appl. No.: 182,032

[22] PCT Filed: Jul. 10, 1992

[86] PCT No.: PCT/NL92/00126

§ 371 Date: Jun. 1, 1994

§ 102(e) Date: Jan. 14, 1994

[87] PCT Pub. No.: WO93/02083

PCT Pub. Date: Feb. 4, 1993

[30] Foreign Application Priority Data

Jul. 18, 1991 [NL] Netherlands ............................ 9101266

[51] Int. Cl.[6] ............................................ C07D 307/77

[52] U.S. Cl. ........................ 549/456; 435/240.4; 435/119; 435/123; 424/195.1

[58] Field of Search ......................... 549/456; 435/240.4, 435/119, 123; 424/195

[56] References Cited

U.S. PATENT DOCUMENTS 5,107,066 4/1992 Ashikawa .................................. 435/41

OTHER PUBLICATIONS

Hominick et al, Diapause In Globodera Rostochienses And . . . , (1985) Nematologica 31, 159–170, E. J. Brill, Leiden.

Spray, F, *Meded.Rijksfac. Landbouwwetensch*, vol. 34, 1969 pp. 550–561.

Alphey, J., Hort. Res., 1981, vol. 21, pp. 169–180.

*Primary Examiner*—Irene Marx

*Attorney, Agent, or Firm*—Keck, Mahin & Cate

[57] ABSTRACT

The invention is directed to a hatching agent for hatching the species and patho types of nematodes causing potation sickness, which nematodes comprise *Globodera pallida*, from the cysts thereof, with a molecular weight of 498, a component $C_{27}H_{30}O_9$ and the structure of formula (a) and the derivatives, esters and salts thereof.

(a)

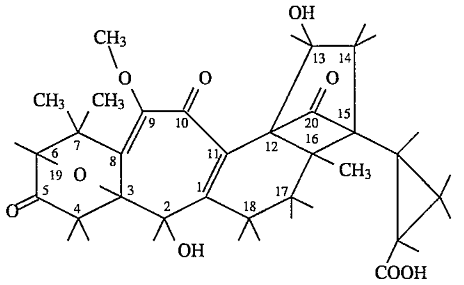

9 Claims, 1 Drawing Sheet

HATCHING AGENT FOR THE POTATO CYST NEMATODE

The present invention relates to a hatching agent for the potato cyst nematode, to a process for preparing such a hatching agent, and to a method of combatting potato sickness.

Potato sickness, that is to say, the attack of the potato plant by the potato cyst nematode (PCN) is a major problem. In particular for the production of industrial potatoes, which is often effected through intensive potato culture, this attack results in a loss in production. In the culture of seed potatoes and consumption potatoes, such an attack also occurs.

The potato plant acts as a host plant to the organisms causing potato sickness: nematodes, at present known by the names of *Globodera rostochiensis* and *Globadera pallida*, of which various pathotypes are known. These nematodes bridge the time in which no potatoes are on the field, i.e., from autumn until spring, or longer if there are no growing potatoes or other host plants, in cysts freely occurring in the soil. These cysts are in fact the hardened abdomens, filled with eggs, of female nematodes of a previous generation. In the spring, when the potato plant is growing, the plant exudes hatching factors which lure the larvae of the nematodes out of the eggs through the cyst wall to the plant.

Preventive measures and possible control of the nematodes have hitherto substantially consisted of intensive crop rotation, measures of farm hygiene, the use of resistant varieties and soil disinfection.

As the financial yield per hectare for potatoes is more favourable than for other crops, intensive crop rotation is little attractive, and where possible, other measures are preferred.

Of the other measures, however, soil disinfection has been the only one so far that found wide application. For this purpose 1,3-dichloropropene and metam sodium are the main disinfectants used. In view of the considerable quantities of disinfectant used, and the chemical, physical, and toxicological properties of these agents, there is a tendency of restricting the use of these agents. The most important reason for it is that these agents are seen as a threat to the environment.

In the past, there has already been a considerable research for agents which artificially effect the hatching of the nematodes. In fact, if one is capable of applying an agent to the soil while out of cultivation, which causes the PCN to hatch, one possibly has an effective biological method of controlling the organism. As, in fact, the nematodes have no source of nutrition in such a situation, they will die, and thereafter potatoes can be cultivated with less chance of damage from potato sickness. By combining such an agent with a small dose of a chemical pesticide, a better effect could also be obtained.

Because, in the past, chemical control was effective, research into the biological method was discontinued without any results being achieved. These investigations were reported, among other publications, in Nematologica, 31, No. 2 (1985), pp 159–170. In it, the use of potato root diffusate for hatching the cysts is mentioned.

In the European patent application No. 434,417 a process for the production of a substance capable of stimulating the hatching of eggs of potato cyst nematodes from the root cells of plants of Solanaceae is described.

It is an object of the present invention to provide a hatching agent for hatching the potato cyst nemerode. The invention relates to an agent for hatching the species and pathotypes of the nematodes causing potato sickness, which nematodes comprise *Globodera rostochiensis* and *Globodera pallida*, among others, from the cysts thereof, with a molecular weight of 498, a composition $C_{27}H_{30}O_9$ and the structure of the following formula:

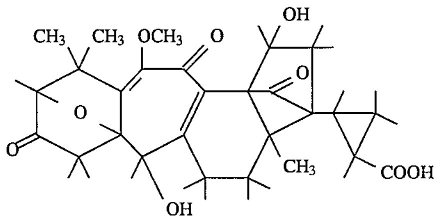

and derivatives, esters and salts thereof.

After extensive and complicated research the above compound has been identified as the component responsible for the hatching of the potato cyst nematode. The systematic name of this compound is trans-2-(2,13-dihydroxy-9-methoxy-7,7,16-trimethyl-5,10,20-trioxo-19-oxahexacyclo [$9.7.0.1^{3,6}.0^{3,8}.1^{12,15}.0^{12,16}$]-eicosa-1(11),8-dien-15-yl)cyclopropanecarboxylic acid.

Figure 1:
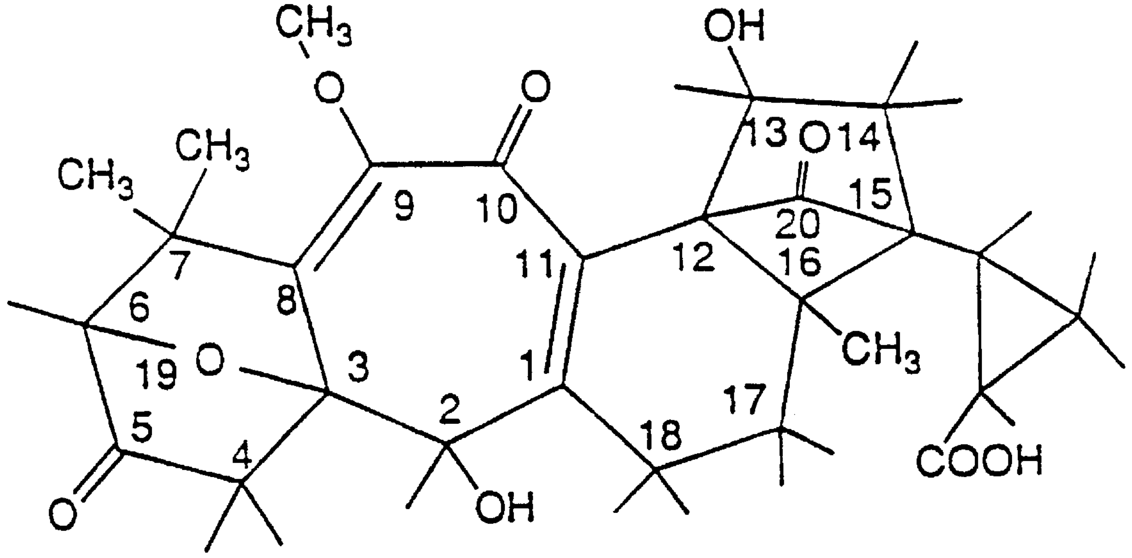
FIG. 1 depicts the chemical structure, including the atomic numbering scheme, of the hatching agent compound.

The spectral data of the pure compound are given in the example.

The hatching agents are non-volatile compounds which are well-soluble in water, methanol, diethyl ether, ethyl acetate and comparable polar solvents, but are insoluble in hexane, dichloromethane, chloroform and the like.

The hatching agent is unstable at pH below 2 and above 7 and at temperatures above about 35° C.

The hatching agent according to the invention can be isolated from a hydroculture, or from a tissue or cell culture of plant parts of members of the nightshade family (Solanaceae), more specifically from potato or tomato roots, in the presence of a suitable nutrient source.

A suitable method of producing a hatching agent for the nematodes referred to is production by means of a-hydroculture of planes of a suitable variety of the Solanaceae or a cell suspension culture of the tissues of such plants.

The hatching agent can also suitably be produced from the recirculating feed water of a substrate culture of members of the Solanaceae family, more in particular tomatoes. Surprisingly it has been found that the recirculating feed water of greenhouse substrate culture of tomatoes, usually on rockwool, contains substantial amounts of the hatching agent.

The hatching agent according to the invention can be obtained, for example, using a cell suspension culture of the tissues of a suitable species variety of the Solaneacea. Using a suitable culture medium, for example as described hereinafter, a solution of the hatching agent is obtained from such a cell suspension. The starting product may be the cell exudate, but it is also possible to use an extract or a homogenate of the cells proper. The cells are taken, for example, from tissues of suitable members of the nightshade family capable of hatching the subject nematodes. Especially important are cultivated varieties of the species *Solanum tuberosum L*, for example, the Mentor variety. It is possible to use the cells as such, or genetically modified cells, for example, cells into which specific genetic information has been introduced using *Agrobacterium tumefaciens*. It is also possible to use shoot cultures, or root cultures, instead of cell suspension cultures. In these methods the same considerations apply with regard to the choice of varieties as applied to the cell suspension cultures.

The media which may be suitable for the production of the hatching agent from a suspension of cells generally comprise:

basal components (salts, spore elements)

carbohydrate source (often sucrose, but it is also possible to use one or more other carbohydrates)

vitamins (vitamin packets are commercially available as standard formulations, and can be used as such)

hormones (a combination often used is cytokinin/auxins, whether or not in combination with gibberellic acid and abscissic acid; however, composition and concentration can be varied depending on the type of cell)

A possible combination of substrate components consists of:

Basal components+vitamins

According to Murshige and Skoog (Physiol. Plant 15, 473–497 (1962)).

Carbohydrate source sucrose solution, for example 30 g/l

Hormones a. In the case of suspension cultures of non-genetically-modified cells, 5 mg/l of naphthyl acetic acid may be added.

b. In the case of non-genetically-modified root cultures, 0.2 mg/l gibberellic acid and 0.05 mg/l naphthyl acetic acid may be added.

c. In the case of cultures on the basis of genetically transformed cells (cell suspension, root or shoot cultures) hormones need non always be used.

Naturally, the above substrate components are just examples of components which may be used, but it is by no means essential that these very components are used. The worker in the art may develop other combinations and compositions resulting in a good hatching agent production on the basis of general knowledge in the art.

Depending on the nature of the culture, various processing procedures may be used to isolate the hatching agent from the culture medium or from the cells. A suitable procedure for isolating the hatching agent from the cells and the extracellular media may comprise the following steps:

1. homogenizing the total cell mass;
2. extraction or precipitation to remove proteins and cell debris;
3. if desired, filtering the liquid phase containing the hatching agent, and diluting or concentrating it to obtain the desired concentration;
4. purifying the liquid phase, using a preparative chromatographic purification method.

Suitable chromatographic purification methods for recovering the hatching agent can be based upon one or more of the following properties of the hatching agent:

solubility in methanol differences in the partition coefficient between water/methanol and water/chloroform systems charge in preparative/analytical chromatography using sepharose hydrophobicity in reversed phase chromatography charge/hydrophobicity ratio in ion exclusion chromatography As indicated above, the hatching agent according to the invention is a non-volatile compound. Owing its low volatility, solutions containing the agent can be effectively concentrated by means of vacuum techniques, such as by means of a rotary film evaporator, and/or freeze drying.

The hatching agent according to the invention can be obtained and used in pure form, that is with a purity of at least 99 wt. %. However, for use this may not be necessary and accordingly in can be obtained and used in partly purified form, for example such as can be obtained from eluting an adsorbent on which the hatching agent has been adsorbed. This is especially useful in case the hatching agent is obtained from the commercial tomato production on substrate in greenhouses. The feed water used in the production, which is recirculated through the greenhouses and supplemented as necessary with fresh water, has been found to contain substantial amounts of hatching agent. It is for example possible to recover the hatching agent continuously or discontinuously from the recirculating water, for example by adsorption or absorption. Elution of the hatching agent results in a concentrated hatching agent with an aqueous solution as carrier.

The hatching agent can be used as such, that is in the acid form, as salt, for example the sodium or potassium salt, as ester with a suitable compound, or as a derivative, a substituted compound and the like.

The hatching agent can be introduced into the soil as such, or in the form of a preparation with a suitable carrier, such as water or an aqueous solution. A solid carrier can also be used.

To obtain a prolonged activity the use of a controlled release formulation can have advantages. Suitable controlled release formulations are well-known, for example such as can be used for components to be used in soil.

Hatching agents in purified or partly purified form are active in aqueous solutions, or as a solid (optionally in formulations) in a concentration ranging from 0.01 to 1000 mg/kg soil, with the optimum ranging from 1 to 100 mg/kg soil.

For best results, the solution or solid, optionally in a formulation, should be introduced or injected into the soil at a depth of preferably about 10–20 cm. On fenny soils, more of the larvae of the PCN are hatched than on other soils, and also significantly more than by spontaneous hatching.

Surprisingly, it has been found that the activity of the hatching agent according to the invention, both in the pure form and in the form of an unpurified preparation from a hydroculture, cell culture or a tissue culture, can be considerably enhanced by using it in an acidic composition, for example in combination with ascorbic acid.

Hatching agent preparations can be tested for activity with reference to the hatching of larvae from eggs.

For this purpose, cysts are cleaned of root fragments and/or dirt and sieved over 0.5 mm and 0.25 mm sieves. 32 mg of the fraction >0.5 and 22.5 mg of the 0.25–0.5 fraction have been weighed: Together this amounts to about 1200 cysts. The solid to be tested is dissolved in tap water to a concentration equivalent to 125 mg/l of the original starting material. Of this stock solution, a 10-fold and a 100-fold dilution are made.

The egg suspension is incorporated in 70 ml tap water and transferred to a graded cylinder and insufflated with air by means of an aquarium pump.

5 ml hatching agent solution and 0.5 ml egg suspension are pipetted into polystyrene tubes and then sealed from the air. As a control, 0.5 ml egg suspension is pipetted into 5 ml tap water. Thereafter the tubes are stored with rotation at 20° C.

Eggs and remaining nematode worms are counted at t=0 days and worms are counted at t=4, 5 and/or 6 days. For this purpose, the tube is first vigorously shaken manually for 4 seconds and then with a Vortex mixer for another 10 seconds. When the suspension has reached quiescence, 0.5 ml is pipetted out of the tube at a level of 1 cm below the liquid surface. This sample is placed on a counting dish and diluted with fresh tap water until the water film covers the entire bottom. The eggs and worms are counted under a binocular.

The calculations were performed as follows: Absolute activity:

$$A_n = \left( \frac{\text{worms}_{t=t} - \text{worms}_{t=0}}{\text{eggs}_{t=0}} \right) \times 100\%$$

$A_n$ = activity of the sample investigated.

The reaction of the free eggs to the presence of hatching agent can be described using the Monod kinetics for the growth of micro-organisms with a non-competitive inhibition of a substrate.

EXAMPLE

About 700 potato plants (of the Mentor variety) were cultured in hydrocultures using a recirculating feed solution containing potassium nitrate, calcium nitrate, potassium dihydrogen phosphate, ammonium sulfate, magnesium sulfate, iron (II) sulfate, mangane (II) sulfate, zinc sulfate, copper (II) sulfate and sodium borate. The phosphate and nitrate contents of the feed solution is measured and, if necessary, adjusted. The pH is kept at a value below 4.2 by adding a solution of 6% nitric acid and 4.25% phosphoric acid, if necessary.

By passing the recirculating feed solution through a column containing Amberlite XAD-2, hatching agent was absorbed on the column.

When changing the feed solution the XAD-2 column is removed and washed with distilled water until the conductivity is below $7\times10^{-6}$ S. The adsorbed material was desorbed from XAD-2 by successively eluting with 60% methanol-water and methanol. The eluate was concentrated and dried by means of a rotary vacuum evaporator and freeze drier.

This hatching agent preparation was subjected to a number of purification steps based upon

- differences of solubility in methanol and water
- partition coefficient in counter-current extraction
- charge in preparative/analytical chromatography using sepharose
- hydrophobicity in reversed phase chromatography
- charge/hydrophobicity ratio in ion exclusion chromatography For this purpose the preparation was dissolved in methanol and shaken until a homogeneous mixture had formed. After centrifugation, the clear supernatant was removed by means of a pipette, and concentrated and dried by means of a rotary vacuum evaporator and freeze drier.

The piping system of a Droplet Counter Current Chromatograph (DCCC) was filled with the top layer of a mixture of chloroform, methanol and water (35:65:40). The hatching agent preparation was dissolved in the top layer of the mixture and introduced into the column. The hatching agents were eluted with the bottom layer of the mixture referred to and collected in fractions. The stationary phase was pumped out of the column, and also collected in fractions. The acivity of the collected fractions of the mobile and stationary phases were tested separately.

Thereafter the fractions were fractionated over an anion exchanger, e.g. Q Sepharose HP. For this purpose, the hatching agent was dissolved and introduced into the column in a buffer (e.g. 5 mM piperazine/acetic acid pH 6.0) and eluted by means of a gradient with another buffer (for example 5 mM piperazine+1M sodium acetate pH 6.0) after the non-bonded material had left the column. The eluate was collected in fractions and tested.

The combined active fractions of the anion exchanger were fractionated over a preparative Rsil C18 column (250× 25 mm) by means of gradient elution. The active fractions were combined, concentrated and freeze-dried. This material was dissolved in 1 mM HCl and fractionated over a HPX-87H column. The active fractions were combined and eluted over two series connected Bakerbond C18 columns. In this way 245 µg pure hatching agent was obtained, which crystalized from a supersaturated solution. The hatching agent thus obtained was subjected to various analyses in order to determine the chemical structure thereof. This resulted in the following structure for the hatching agent:

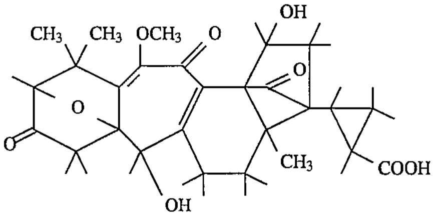

This hatching agent had a $K_m$ value, as defined in accordance with the Monod kinetics of about $10^{-8}$ g/l. Based upon this value the hatching agent content of the unpurified solutions can be determined using the equation:

$$\text{Hatching agent content} = \frac{10^{-8}}{K_m} \times 100\%$$

in which $K_m$ is the concentration value at which half of the maximum hatching by the unpurified agent has been found.

Spectral analyses of hatching agent

Mass spectrometry

The analyses of purified hatching agent were performed with Finnigan MAT-95Q, Finnigan MAT TSQ 700 MS/MS and Finnigan MAT Laser TOF mass spectrometers.

The mass-spectrum of the material in acid form yielded the molucule ion having a molecular weight of 498 and a number of fragments with mass/charge of 480, 470 and 450 Dalton. The electrospray and laser desorption mass-spectrum of the sodium salt gave a mass/charge of 521 Dalton.

Proton NMR

The hatching agent was dissolved in 0.5 ml $D_2O$ and placed in a Varian-400 spectrometer. The scanning time was about 15 hours (4720 transients). A spectrum was also made from a comparable control.

In the proton NMR spectrum, the following shifts and couplings were found, using a Varian-Unity 400 MHz spectrometer in $D_2O$ at 5° C., external reference sodium salt of 3-(methylsilyl)-propionic acid-$d_4$, 0.0 ppm. The sample was used as the sodium salt:

| Carbon position | Shift (ppm) | Couplings (Hz) |
|---|---|---|
| 2 | 4,09 | — |
| 4 | 2,61 | 17,90 (4') |
| 4' | 2,61 | |
| 6 | 4,04 | — |
| 7 (Me) | 1,20 | — |
| | 1,21 | — |
| 9 (OME) | 3,26 | — |
| 13 | 4,32 | 7,68 (14) 2,74 (14') |
| 14 | 2,18 | 7,54 (13) 12,47 (14') |
| 14' | 2,04 | 12,60 (14) 3,02 (13) |
| 16 (Me) | 1,34 | — |
| 17 | 1,95 | 4,94 (18') 14,47 (17') |
| 17' | 1,43 | 5,21 (18) 13,57 (17') + ? (18') |
| 18 | 2,48 | 5,21 (17') 20,43 (18') |
| 18' | 2,58 | pattern unclear |
| | Cyclopropane moiety | |
| 1 | 1,78 | multiplet |
| 2 | 1,50 | multiplet |
| 3 | 0,85 | doublet |
| 3' | 0,84 | dubbel doublet |

Infrared analysis

Pure hatching agent was dissolved in methanol and transferred to a KBr filled microcup. After careful evaporation the spectrum was determined. As blanc pure methanol was prepared in the same manner. The spectra have been determined using a Bruker IFS-85 FTIR spectrometer, DTGS detector, optical resolution 4 $cm^{-1}$, number of scans 128/256. The spectrum was transformed using the Kubella-Munk transformation. The absorption bands could be assigned as follows:

| Wavenumber ($cm^{-1}$) | Functional group |
|---|---|
| 3379 | —OH, including $H_2O$ |
| 2949/1470 | —$CH_3$ and/or $CH_2$ in 5-ring |
| 2838 | —$OCH_3$ |
| 1765 | >C═O in 4-ring |
| 1660 | C═C |
| Complex bonds in 1200-100 | Various aliphatic ether-oxygen atoms |

UV

The UV spectrum of the hatching agent is characterized by an absorption maximum at 267 nm and one at about 200 nm. The ratio of the extinctions at 225 nm and 267 nm is about 1.5 for the pure hatching agent. The extinction coefficient at 267 nm is 4550±1250 $l.mol^{-1}$. This absorption suggests the presence of a conjugated system of C═C and/or C═O bonds, which corresponds with the structure of the hatching agent of the invention.

Röntgen diffraction analysis

The crystal was measured on an Enraf-Nonius CAD-4 diffractometer with graphite-monochromated CuKα radiation and α-2θscan. A total of 10551 reflections was measured within the range $-13 \leq h \leq 13$, $-25 \leq k \leq 0$, $-14 \leq l \leq 14$, the unique set consits of 5257 reflections. Of these, 3721 were above the significance level of 2.5 σ(I). The maximum value of (sinθ)/λ was 0.61 $Å^{-1}$. Two reference reflections (021,200) were measured hourly and showed 9% decrease during the 116 h collecting time, which was corrected for. Unit-cell parameters were refined by a least-squares fitting procedure using 23 reflections with 74<2θ<84°. Corrections for Lorentz and polarisation effects were applied. The structure was solved by the program CRUNCH, which uses Karle-Hauptman matrices to determine the phases. The water molecules were found in a subsequent ΔF synthesis. Anisotropic block-diagonal least-squares refinement on F, converged to R=0.126, $R_w$=0.171, $(\Delta/\sigma)_{max}$=0.85. The goodness of fit S=0.548. A weighting scheme $w=(3.0+F_{obs}+0.011*F_{obs}^2)^{-1}$ was used. An empirical absorption correction (DIFABS, Walker and Stuart 1983) was applied, with coefficients in the range of 0.23–1.43. Scattering factors were taken from Cromer and Mann (1968); *International Tables for X-ray Crystallography* (1974). All calculations were performed with XTAL (Hall and Stewart 1990), unless stated otherwise. The atomic numbering scheme is shown in FIG. 1.

We claim:

1. A hatching agent composition consisting essentially of a compound of the following formula:

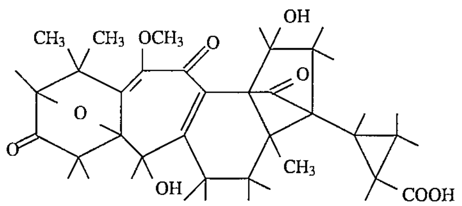

or a salt or an ester of the compound as the active ingredient to effect hatching of potato cyst nematodes, said active ingredient having been isolated from the recirculating feed water of a culture of a plant of the family Solanaceae.

2. The composition of claim 1 wherein said active ingredient is isolated from said recirculating feed water by adsorption of the active ingredient on a chromatographic column and thereafter eluting the active ingredient from said column.

3. The composition of claim 2 wherein the active ingredient is eluted from the column with an aqueous solution.

4. The composition of claim 1 in combination with a carrier.

5. The composition of claim 4 wherein said carrier is water or an aqueous solution.

6. The composition of claim 4 wherein said carrier is a solid.

7. The composition of claim 1 wherein the culture is of tomatoes or potatoes.

8. A hatching agent composition consisting essentially of a compound of the following formula:

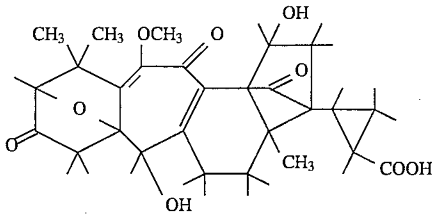

or a salt or an ester of the compound as the active ingredient to effect hatching of potato cyst nematodes, said active ingredient having been isolated from the recirculating feed water of a culture of a plant of the family Solanaceae and wherein said active ingredient has a purity of at least 99 wt. %.

9. A hatching agent composition consisting essentially of a compound of the following formula:

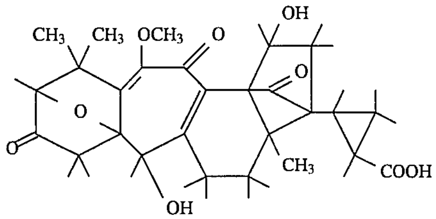

or a salt or an ester of the compound as the active ingredient to effect hatching of potato cyst nematodes, said active ingredient having been isolated from the recirculating feed water of a culture of a plant of the family Solanaceae, in combination with soil disinfectants selected from the group consisting of metam sodium and 1,3-dichloropropene.

* * * * *